US012624331B2

(12) United States Patent
Grant et al.

(10) Patent No.: US 12,624,331 B2
(45) Date of Patent: May 12, 2026

(54) BIOREACTOR INCLUDING PROBE FOR ELECTRICAL OR ELECTROMAGNETIC MEASUREMENTS

(71) Applicant: The Automation Partnership (Cambridge) Ltd., Royston (GB)

(72) Inventors: Paul Grant, Royston (GB); Adrian Salariu, Royston (GB); Jochen Scholz, Gottingen (DE); Stuart Tindal, Gottingen (DE)

(73) Assignee: THE AUTOMATION PARTNERSHIP (CAMBRIDGE) LTD., Royston (GB)

( * ) Notice: Subject to any disclaimer, the term of this patent is extended or adjusted under 35 U.S.C. 154(b) by 496 days.

(21) Appl. No.: 18/030,696

(22) PCT Filed: Oct. 5, 2021

(86) PCT No.: PCT/EP2021/077401
§ 371 (c)(1),
(2) Date: Apr. 6, 2023

(87) PCT Pub. No.: WO2022/078815
PCT Pub. Date: Apr. 21, 2022

(65) Prior Publication Data
US 2023/0374436 A1 Nov. 23, 2023

(30) Foreign Application Priority Data
Oct. 15, 2020 (EP) ..................................... 20202136

(51) Int. Cl.
*C12M 1/00* (2006.01)
*C12M 1/34* (2006.01)

(52) U.S. Cl.
CPC ............ *C12M 41/00* (2013.01); *C12M 23/26* (2013.01); *C12M 23/28* (2013.01); *C12M 23/38* (2013.01); *C12M 41/26* (2013.01)

(58) Field of Classification Search
CPC ...... C12M 41/00; C12M 23/26; C12M 23/28; C12M 23/38; C12M 41/26
See application file for complete search history.

(56) References Cited

U.S. PATENT DOCUMENTS 6,670,817 B2 * 12/2003 Fournier .............. G03G 15/086
324/662
2007/0272028 A1 * 11/2007 Fujimoto .............. G01L 19/003
73/756

(Continued)

FOREIGN PATENT DOCUMENTS

DE 202016000554 U1 5/2017
KR 101 910 118 B1 10/2018

OTHER PUBLICATIONS

International Search Report and Written Opinion, International Application No. PCT/EP2021/077401, European Patent Office-Searching Authority, mailed Jul. 1, 2022, 9 pages.

*Primary Examiner* — Liban M Hassan
(74) *Attorney, Agent, or Firm* — Quarles & Brady LLP

(57) ABSTRACT
A bioreactor includes a rigid-walled vessel for containing a biological medium, the vessel having a lid. The bioreactor further includes a probe passing through an aperture in the lid and having a sensing end inside the vessel and a remote end outside the vessel. The sensing end has plural electrodes for immersion in the biological medium, and the remote end is configured for coupling to external devices and transmission thereto of electrical or electromagnetic measurements made by the electrodes. One of the lid and the probe has one or more resiliently deformable mechanisms and the other of the lid and the probe has one or more respective comple- (Continued)

mentary surfaces. The resiliently deformable mechanisms and the complementary surfaces are configured such that, on insertion of the probe through the aperture to assemble the probe to the lid, the one or more resiliently deformable mechanisms are first deformed on sliding against the one or more complementary surfaces and then resile when the probe reaches a predetermined insertion position relative to the lid to secure the probe to the lid. One of the lid and the probe carries a sealing element which seals the probe to the lid when the probe is secured at the predetermined position.

12 Claims, 11 Drawing Sheets

(56) References Cited

U.S. PATENT DOCUMENTS

2012/0329151 A1 * 12/2012 Baskar ................... C12M 23/14
                                                                    435/351
2016/0281046 A1 *  9/2016 Bargh .................... C12M 23/44
2018/0224386 A1 *  8/2018 Furey .................... G01N 27/07

* cited by examiner

250

254

252

BIOREACTOR INCLUDING PROBE FOR ELECTRICAL OR ELECTROMAGNETIC MEASUREMENTS

RELATED APPLICATIONS

This application is a 35 U.S.C. § 371 national phase application of PCT/EP2021/077401 (WO-2022/078815-A1), filed on Oct. 5, 2021, entitled "BIOREACTOR INCLUDING PROBE FOR ELECTRICAL OR ELECTROMAGNETIC MEASUREMENTS", and claims priority to EP-20202136.6 filed on Oct. 15, 2020, both of which are incorporated herein by reference in their entirety.

This application claims priority from EP 20202136.6 filed 15 Oct. 2020, the contents and elements of which are herein incorporated by reference for all purposes.

FIELD OF THE INVENTION

The present invention relates to a bioreactor including a probe for electrical or electromagnetic measurements.

BACKGROUND

Cell culture is a process for growing cells in an artificial environment such as a bioreactor. Often, the cells are grown whilst suspended in a culture growth medium. Monitoring and/or controlling the environment to which the cells are exposed in the bioreactor is important in order to control the physiology of the cells and the amount of target produced. Specifically, the monitoring of various parameters of the cells and/or the culture growth medium within the bioreactor is key to their control.

Example bioreactor systems suitable for cell culture are described in US 2016/0152936 and WO 2014/020327.

Monitoring of parameters of the cells can be achieved offline by taking samples and/or in-line by measuring various characteristics of the cells directly in the process. In-line monitoring is becoming increasingly important, as it facilitates process control and process automation. In-line monitoring generally uses a sensor inserted directly into the culture growth medium contained in a vessel. For example, electrical or electromagnetic measurements made by electrodes immersed in growth media can be used to measure quantities such as capacitance, impedance, permittivity, conductivity etc. These measurements may then be subject to analysis techniques such as impedance spectroscopy in order to derive, for example, cell concentration.

Probes carrying such electrodes need to be arranged so that they can be connected to electronics and communications outside the vessel bioreactor, while ensuring that the sensing end of the probe is properly immersed in the cell culture in the vessel.

Other considerations are: speed of assembly, and low risk of introducing contaminants into the cell culture The present invention has been devised in light of the above considerations.

SUMMARY OF THE INVENTION

The present invention provides a bioreactor including:
a rigid-walled vessel for containing a biological medium, the vessel having a lid;
a probe passing through an aperture in the lid and having a sensing end inside the vessel and a remote end outside the vessel, the sensing end having plural electrodes for immersion in the biological medium, and the remote end being configured for coupling to external devices and transmission thereto of electrical or electromagnetic measurements made by the electrodes;
wherein one of the lid and the probe has one or more resiliently deformable mechanisms and the other of the lid and the probe has one or more respective complementary surfaces, the resiliently deformable mechanisms and the complementary surfaces being configured such that, on insertion of the probe through the aperture to assemble the probe to the lid, the one or more resiliently deformable mechanisms are first deformed on sliding against the one or more complementary surfaces and then resile when the probe reaches a predetermined insertion position relative to the lid to secure the probe to the lid; and
wherein one of the lid and the probe carries a sealing element which seals the probe to the lid when the probe is secured at the predetermined position.

By securing the probe to the vessel through the lid in this way, correct location of the sensing end in the vessel can be assured, even though the probe is a non-integral part of the lid, or indeed of the vessel. Moreover, assembly by insertion through the lid of the vessel and mechanical joining via the resiliently deformable mechanisms and complementary surfaces is compatible with fast assembly. The mechanical joining approach also allows glues or other adhesive-based fixing techniques to be avoided, such techniques carrying risks of contamination by contact of the cell culture with glues or glue residuals.

Optional features of the present invention will now be set out. The invention includes the combination of the optional features described except where such a combination is clearly impermissible or expressly avoided.

Conveniently, the one or more resiliently deformable mechanisms and the one or more complimentary surfaces may form a snap-fit connector.

The one or more resiliently deformable mechanisms may be one or more flexible members, for example formed of flexible plastic. Another option, however, is for the resiliently deformable mechanisms to be one or more spring-loaded detent mechanisms, e.g. in which the or each resiliently deformable mechanism has a substantially rigid (non-flexible) contact member which slides against its respective complementary surface, and a spring which biases the contact member in a direction towards the complementary surface while accommodating movement of the contact member in an opposite direction.

The probe and the lid may be configured such that the one or more resiliently deformable mechanisms are deformable by a user to allow the probe to be withdrawn from the lid and reinserted multiple times.

For example, the resiliently deformable mechanisms may have features which are accessible manually or by a tool so that a force can be applied to the or each mechanism which re-deforms that mechanism allowing withdrawal. This is particularly useful in the context of a snap-fit connector, which otherwise may be impossible to withdraw without damaging the mechanism.

Conveniently, the lid and the probe may have respective abutment surfaces which interact to prevent the probe being over-inserted beyond the predetermined position. In such an arrangement, the sealing element may be sandwiched between and seal to the abutment surfaces to seal the probe to the lid when the probe is located at the predetermined position.

The sealing element may be, for example, a gasket or an elastomeric sealing element such as O-ring.

The probe and the aperture may be keyed such that the probe can adopt only one angular (i.e. rotational) orientation around the insertion direction of the probe when the probe is located at the predetermined position. For example, if the sensing end is configured to make the electrical or electro-magnetic measurements along a sensing direction which is not the insertion direction of the probe (for example it may be 90° to the insertion direction), the probe can then be secured with the sensing direction correctly aligned around the insertion direction, e.g. pointing into the centre of the vessel for a probe that is assembled off-centre in the vessel.

The probe may have a lateral projection at its sensing end which rests against a side wall of the vessel to enforce a minimum stand-off distance between the probe and the side wall along the length of the probe from the lid to the projection. In this way, undesirable accumulation of biomass solids between the probe and the side wall can be avoided. Preferably, the minimum stand-off distance is at least 1.0 mm.

Conveniently, the probe may be part of a multi-purpose assembly inserted through the aperture in the lid, the multi-purpose assembly also containing either or both of (a) a sparger for conveying sparging gas to the biological medium, and (b) further electrodes forming a pH sensor for sensing the pH of the biological medium. In this way, fewer assembly steps may be needed to form the finished biore-actor.

The lid may be removably replaceable from the vessel.

The bioreactor may be a single-use bioreactor. In this case, the lid may be an integral part of the vessel, i.e. non-removably replaceable.

The probe may be a capacitance, impedance, permittivity or conductivity probe. Typically the electrical or electro-magnetic measurements made by the electrodes are per-formed at high AC frequency. For example, they may be performed in or over a defined frequency range (e.g. 10 kHz to 40 MHz).

SUMMARY OF THE FIGURES

Embodiments and experiments illustrating the principles of the invention will now be discussed with reference to the accompanying figures in which.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
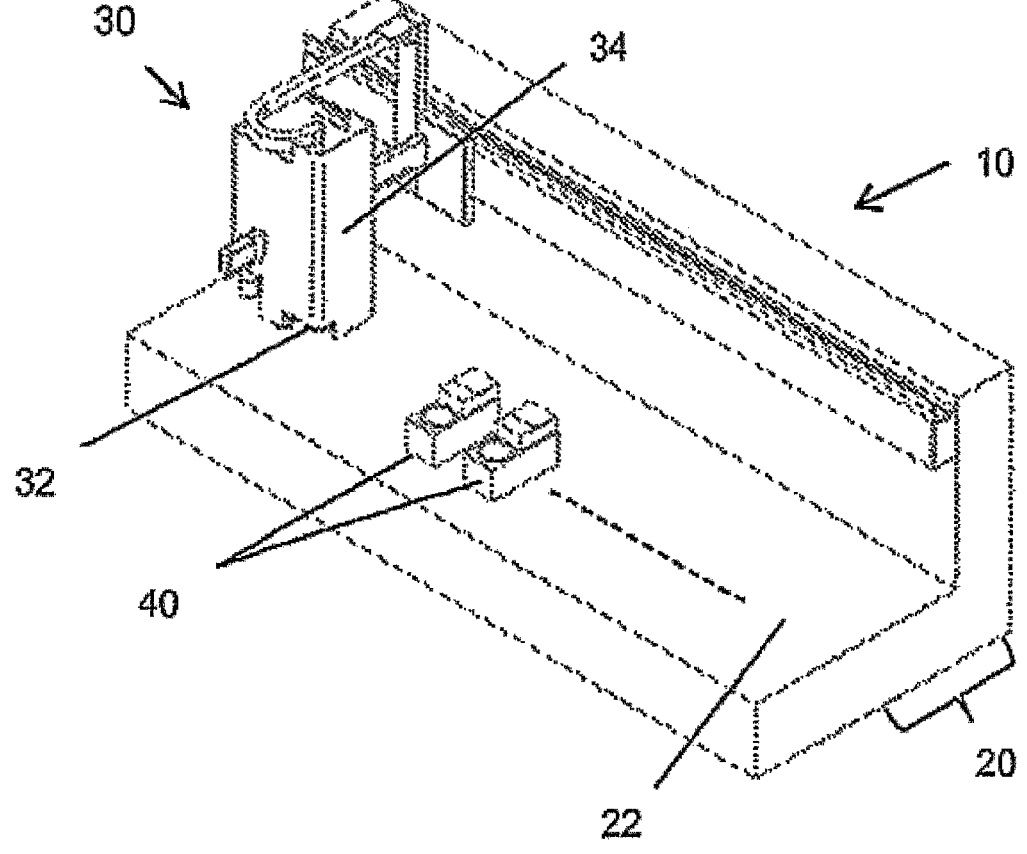
FIG. 1 is a perspective overview of an automated macro-scale bioreactor system.

An automated macro-scale bioreactor system 10 com-prises, generally, a bed station 20 and a liquid handling station 30, which may be interconnected (as shown in FIG. 1) or may be separate from one another. The bed station 20 comprises a platform 22 on which are mounted various modules. The modules include at least one cell culture bioreactor 40. The liquid handling station 30 includes a head 32 mounted on a conventional X-Y positioning robot 34. The head 32 includes components that are selectively move-able along the Z axis. The head 32 is thus capable of addressing and interacting with each of the modules.

Figures 2A, 2B, 2C:
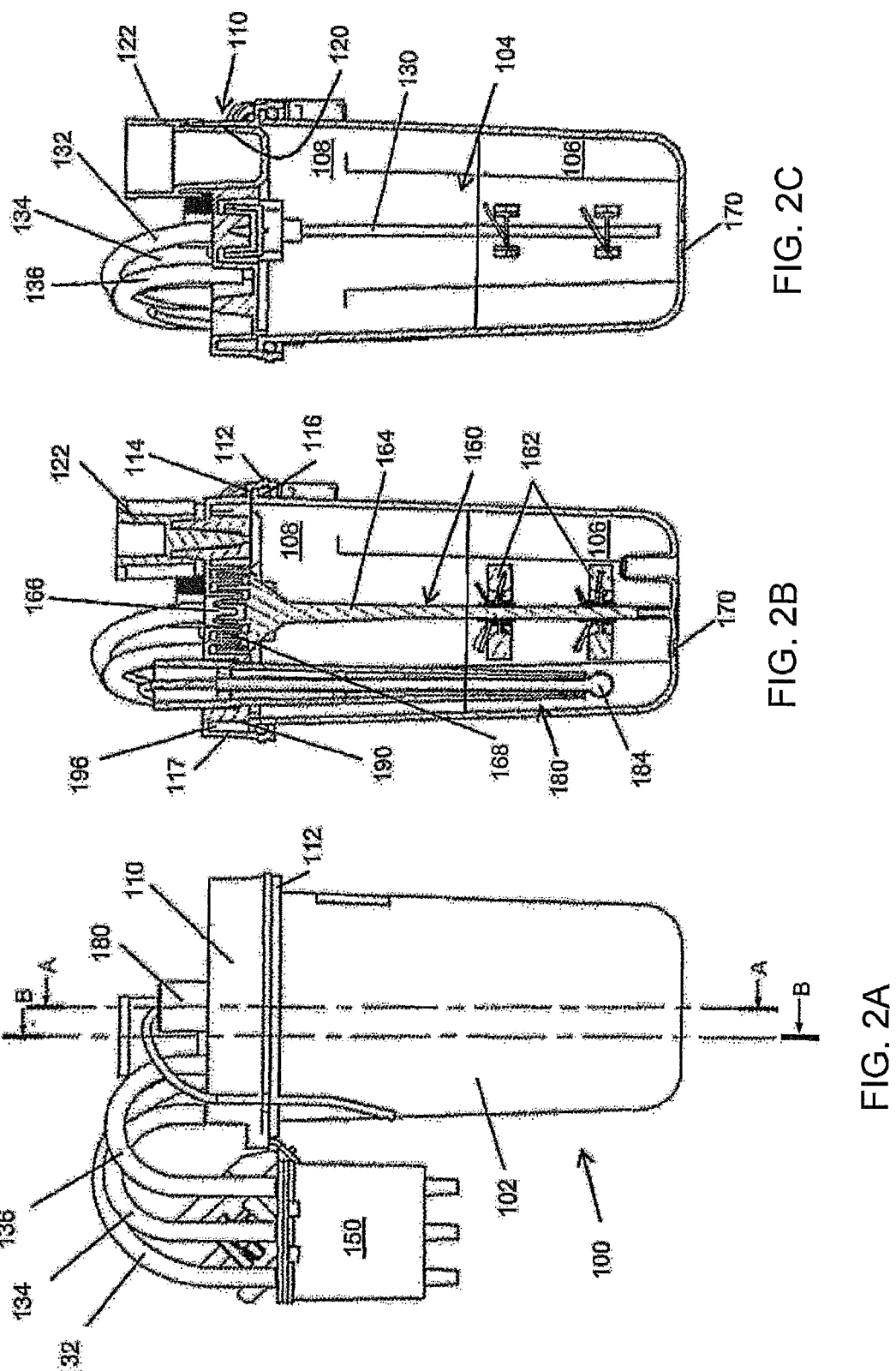
FIG. 2A is a side elevation of a bioreactor vessel and associated filter module, for use in the system of FIG. 1.
FIG. 2B is a cross-section through A-A of FIG. 2A.
FIG. 2C is a cross-section through B-B of FIG. 2A.

Each cell culture bioreactor 40 generally comprises a receiving station for removably receiving and providing temperature control of a rigid-walled bioreactor vessel 100 shown in FIGS. 2A-2C. The bioreactor vessel 100 for use with the bioreactor system 10 comprises a vessel 102 defining a chamber 104 for receiving a cell culture solution 106 having a headspace 108 above. The vessel is typically a macro-scale vessel, which is to say it holds a working volume of approximately 250 ml of cell culture solution 106. It will be understood, however, that the principles described with reference to this scale of vessel may be applied, mutatis mutandis, to both larger- and smaller-scale vessels.

The vessel further comprises a lid 110 secured to the top of the vessel 102 by a friction fit between a skirt 112 overlapping a circumferential lip 114 on the upper edge of the vessel 102. An O-ring 116 is retained between the skirt 112 and an outer wall below the lip 114 to provide a seal between the lid 110 and the vessel 102. The lid 110 includes a fluid transfer port 120, on which is removably attached a cap 122. A sparge tube 130 has a distal end opening in the cell culture solution 106 and a proximal end terminating at a port through the lid 110. A gas input line 132 is connected at one end to the port and at the other end to a fluids module 150 and may include a filter (not shown).

A stirrer 160 comprising blades 162 mounted at the base of a vertical shaft 164 is rotatably mounted within the vessel 100. The upper end of the shaft 164 includes a drive input 166, and is retained within the lid 110 by means of a labyrinth seal arrangement 168. The drive input 166 is connected to a drive train (not shown) which is powered by a motor (not shown) housed in the cell culture bioreactor 40. The vessel may include a sensor spot 170 (e.g. a DO sensor spot to detect the dissolved oxygen levels of the solution) disposed on a bottom wall of the vessel 102 to detect the dissolved oxygen levels of the solution 106 and to be interrogated from the exterior of the vessel 100. The vessel may include a pH electrode sensor probe 180 which is received in a port in the lid 110. A distal end 184 of the probe 180 extends into the vessel chamber 104 so as to be covered, in use, by the cell culture medium 106 for monitoring the pH level of the medium in a known manner.

The fluids module 150, in addition to the gas input line 132 to the sparge tube 130, may include a further gas line 136. Gas line 136 is a second input line, connected to a port through the lid 110 for delivery of gases into the headspace 108. This input line 136 may also include a filter (not shown). The fluids module 150 may be respectively connectable to O₂, N₂ and CO₂ gas supplies for selective controlled delivery of those gases, alone or in combination, to the vessel via the input lines 132 and 136.

A groove may be provided in a lower surface of the lid 110 to define a circumferentially arranged conduit 196 through which fluids evaporated from the headspace 108 can be transported to an outlet line 134, and thence to the fluids module 150. This outlet line 134 may also be provided with a filter (not shown), and is typically connected to sensors (not shown) for monitoring the gas and water content of the outlet fluid to provide an indicator of metabolic activity in the cell culture 106.

Developments of the bioreactor described above are fitted with other probes in addition to or in place of the various probes discussed above. In particular, a bioreactor of the present invention is fitted with a probe for making electrical or electromagnetic measurements on the cell culture solution. From these measurements it is possible to derive characteristics of the cell culture solution, such as cell concentration. For convenience, in the following we refer to the probe as a capacitance probe, but it will be understood that such a probe is not limited to make capacitance measurements and can be used to make measure e.g. impedance, permittivity or conductivity. In FIGS. 3-11 discussed below, features which are the same or correspond to features in FIGS. 1 and 2A-2C are denoted with the same references numbers.

Figure 3:
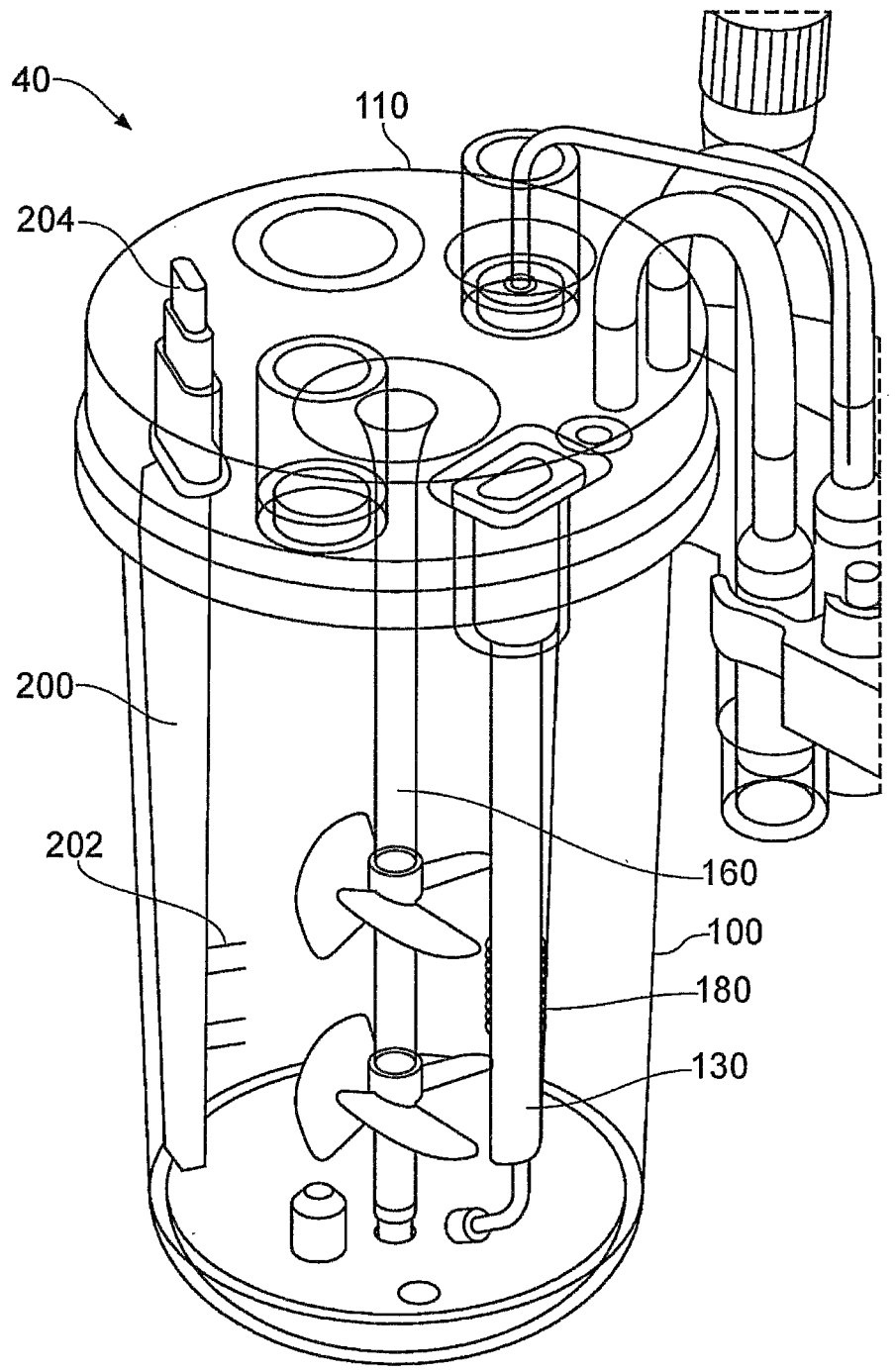
FIG. 3 is a transparent, perspective view of a bioreactor having a capacitance probe.

FIG. 3 shows a transparent, perspective view of a bioreactor 40 having a capacitance probe 200, and suitable for use in the automated bioreactor system 10. The capacitance probe passes through an aperture in the lid 110. The aperture in this case is offset from the centre of the lid, but a centrally disposed aperture and probe may also be deployed, e.g. with the stirrer 160 replaced by a different stirring arrangement. Just the lid of the vessel 100 and the capacitance probe are shown in transparent, perspective view in FIG. 4, detail of the capacitance probe as it passes through the lid is shown in cross-sectional view in FIG. 5, and a transverse cross-section through the bioreactor is shown in FIG. 6.

Figure 4:
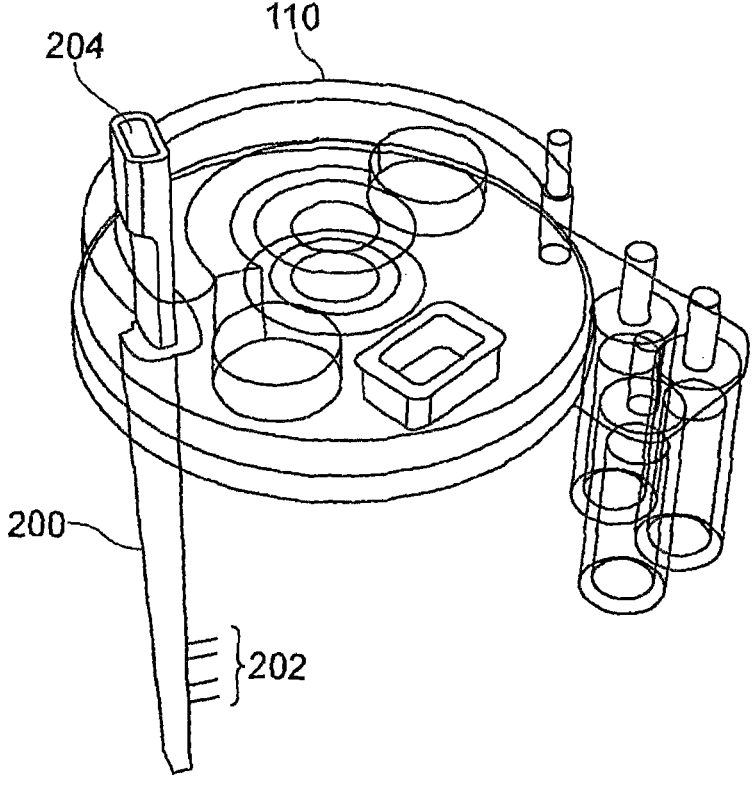
FIG. 4 is a transparent, perspective view of the capaci-tance probe, and a lid of a vessel of the bioreactor of FIG. 3.

The capacitance probe 200 has a sensing end inside the vessel and a remote end outside the vessel. The sensing end has four electrodes 202 (although other numbers of electrodes are possible) for immersion in the cell culture solution. The electrodes may be inwardly directed towards the centre of the vessel 100, as shown, or at other predetermined orientations. Another option, however, is for the electrodes to be non-directional ring electrodes. The remote end has a connector 204 configured for coupling to external devices and onward transmission of measurements made by the electrodes. A male form of the connector 204 is shown in FIG. 3, while a variant female connector is shown in FIG. 4.

The capacitance probe 200 is assembled to the lid 110 by inserting the remote end through the aperture from the underside of the lid. The aperture is surrounded by a collar 205 having a resiliently deformable lip 207 at the top end thereof, the lip producing a slight reduction in the cross-sectional area of the aperture. The probe has a pair of protuberances 206 on each side of the remote end, the protuberances of each pair being spaced apart in the insertion direction of the probe. On insertion of the probe through the aperture, the protuberances travel up the collar until the top protuberance of each pair reaches the lip. The reduction in the cross-sectional area of the aperture at the lip then causes the top protuberances to slide against inwardly-facing surfaces of the lip, which is deformed outwards by the passage of the protuberances. When the probe reaches a predetermined insertion position at which the top protuberances exit the aperture above the lip while the bottom protuberances of each pair are still located just below the lip, the lip resiles inwards and is trapped in the spaces between the pairs of protuberances, preventing the probe from being pulled or falling back through the aperture.

By securing the non-integral capacitance probe 200 to the vessel through the lid 110 in this way, correct vertical location of the electrodes 202 of the sensing end in the vessel 100 can be assured. Moreover, the assembly can be performed speedily and without recourse to glues which could contaminate the cell culture. Nonetheless, by supplying a sufficient downwards force on the probe, the insertion operation can be reversed and the probe removed from the lid. Thus the probe can be easily replaced or substituted.

Figure 5:
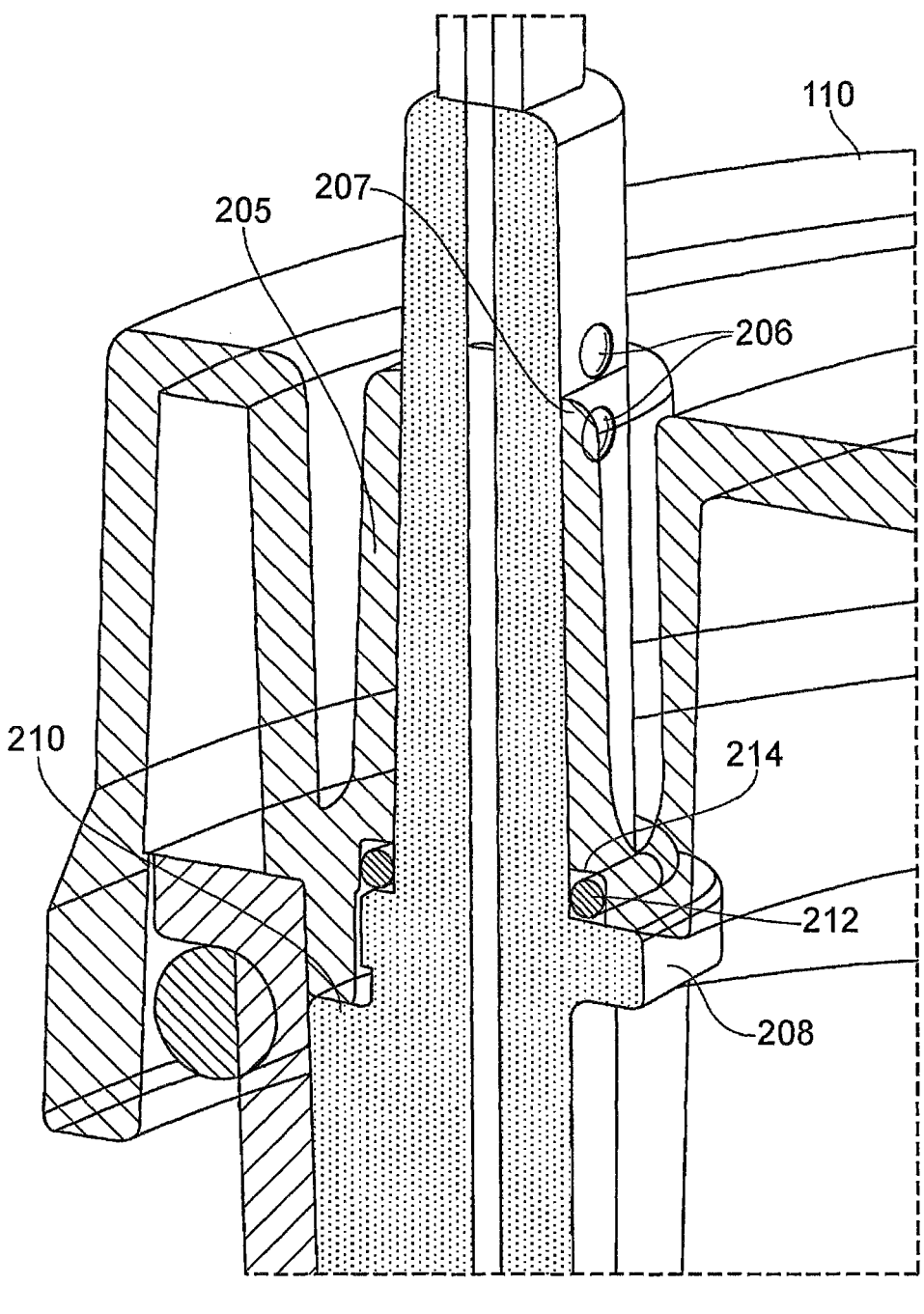
FIG. 5 shows a cross-sectional view of detail of the capacitance probe of FIGS. 3 and 4 as it passes through the lid.
Figure 6:
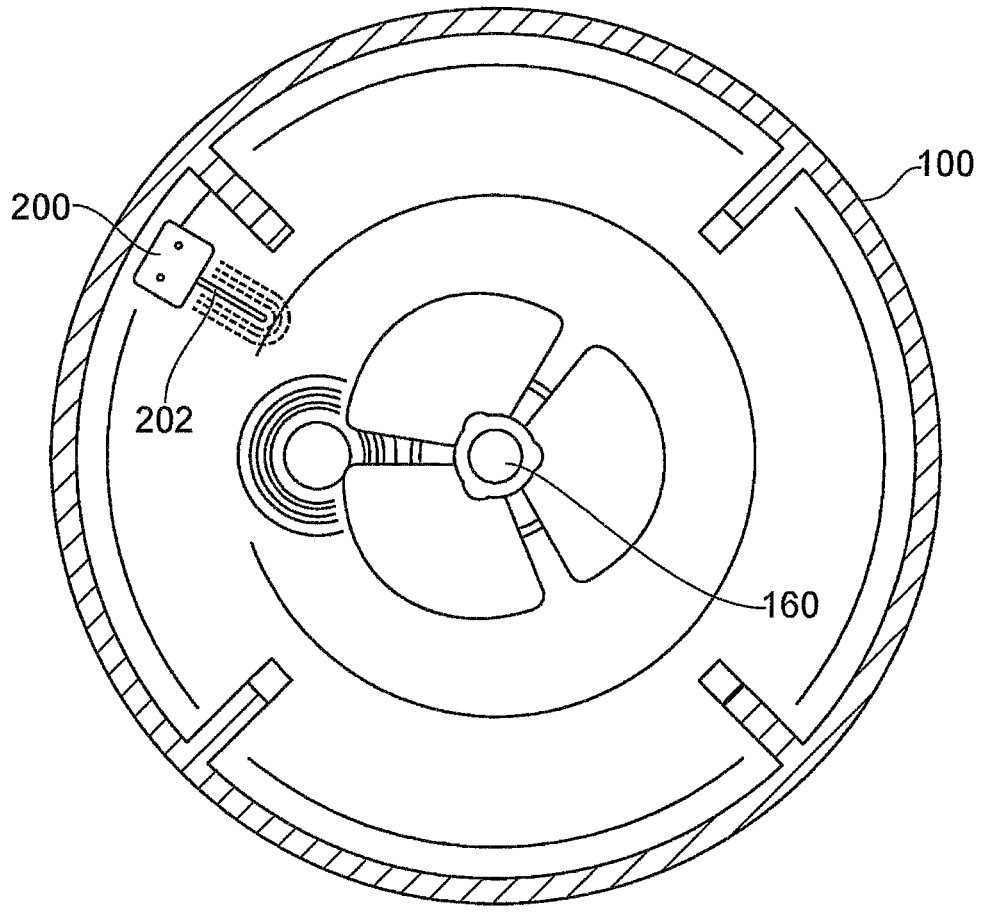
FIG. 6 shows a transverse cross-section through the bioreactor of FIGS. 3 to 5.

As best shown in FIG. 5, the capacitance probe 200 has a flange 208 at one side and a shoulder 210 at an opposite side which form respective top surfaces that abut corresponding under surfaces of the lid 110 to prevent over-insertion of the probe beyond the predetermined insertion position. In addition, the capacitance probe 200 carries a sealing ring 212 on a top surface of the flange 208. The sealing ring locates into a correspondingly-shaped groove 214 which surrounds the entrance to the aperture at the underside of the lid 110, and is squeezed between an outwardly-facing surface of the probe and an inwardly facing surface of the lid to seal the probe to the lid when the probe is secured at the predetermined position.

As noted above, the electrodes 202 may be inwardly directed towards the centre of the vessel 100, as illustrated in FIG. 6 which shows a cross-section through the bioreactor 40 at the height of one of the electrodes. The electric field around the electrodes is indicated by dashed lines. This predetermined orientation of the electrodes avoids helps to ensure there are no obstacles in the vicinity of the electrodes which could affect measurements on the cell culture solution made by the electrodes. The predetermined orientation of the electrodes can be imposed by keying the capacitance probe 200 and whereby the probe can adopt only one angular (i.e. rotational) orientation around the insertion direction of the probe. Thus, the probe and the aperture have a corresponding racetrack shaped cross-section, which of itself allows just two (180° apart) insertion orientations of the probe in the aperture. However, only one of these insertion orientations is actually usable due to the configuration of the flange 208 and the shoulder 210 of the probe. More particularly, these are offset from each other in the insertion direction of the probe, such that, were the probe in the wrong orientation, the flange would interfere with the abutment surface of the lid 110 for the shoulder and prevent full insertion.

In a variant of the bioreactor of FIGS. 3 to 6, rather than having rigid protuberances 206 and a resiliently deformable lip 207, the relative stiffnesses of the protuberances and the lip can be swapped such that when the top protuberances slide against inwardly-facing surfaces of the lip, the protuberances are deformed inwards by the passage through the lip. When the top protuberances exit the aperture above the lip, the top protuberances then resile outwards. Indeed, a similar mode of operation can be obtained by exchanging the protuberances for detent mechanisms, each mechanism comprising a spring loaded ball bearing that, in an un-inserted state of the probe protrudes from the surface of the probe, but is depressable inwards against the resistance of an internal restoring spring.

Figure 7:
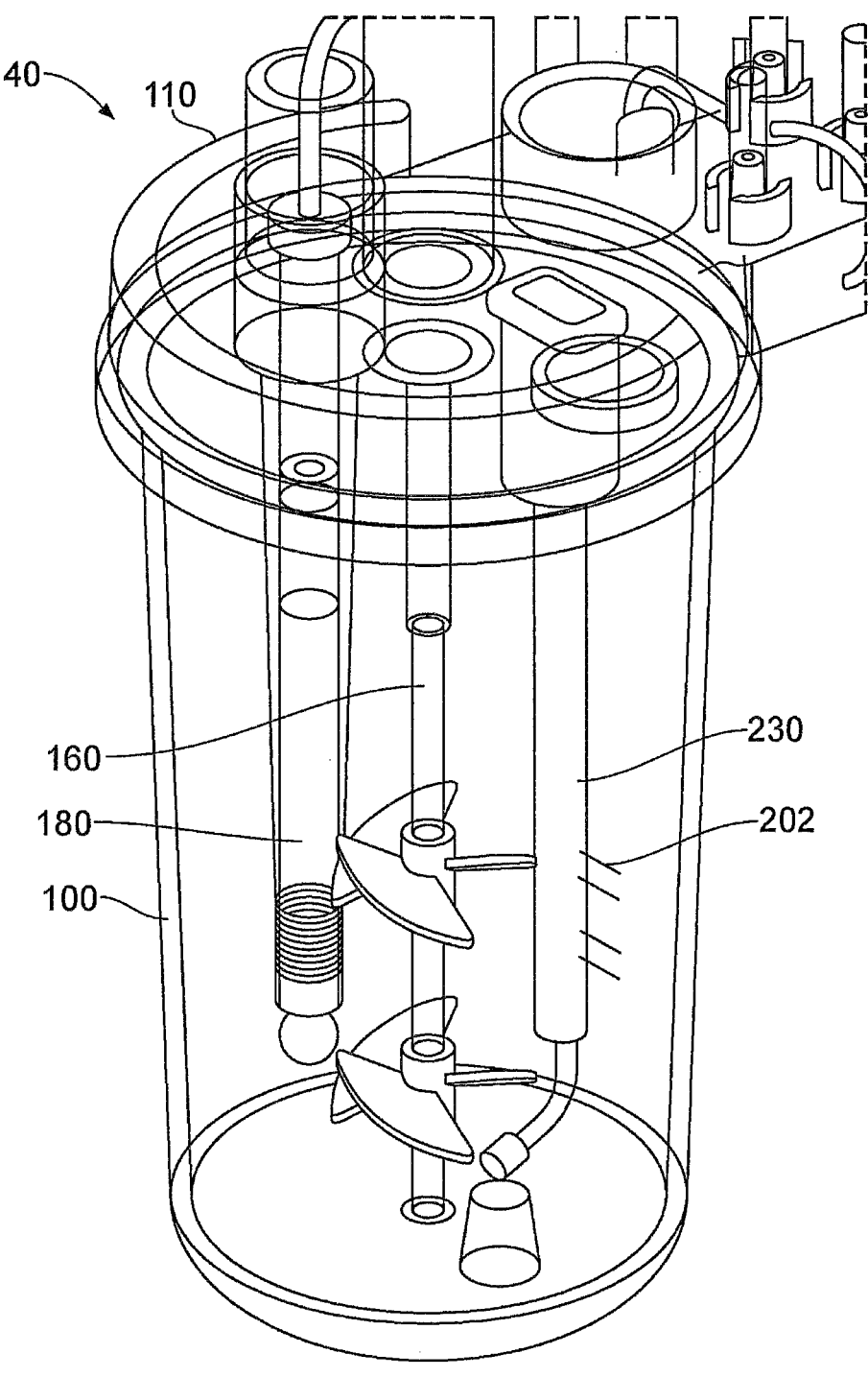
FIG. 7 is a transparent, perspective view of a variant bioreactor having a capacitance probe which is part of a multi-purpose assembly.
Figure 8:
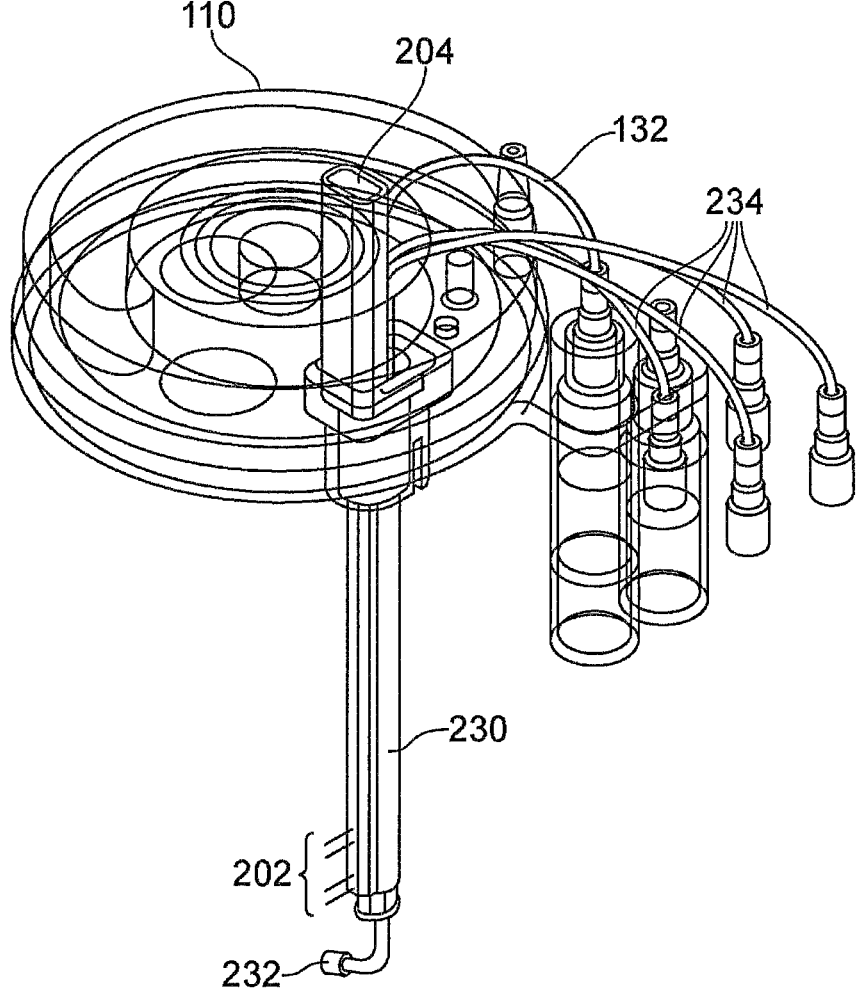
FIG. 8 is a transparent, perspective view of the multi-purpose assembly, and a lid of a vessel of the bioreactor of FIG. 7.

FIG. 7 shows a transparent, perspective view of a further variant bioreactor 40. In this variant the capacitance probe is integrated with a sparge tube and liquid feed tubes to form a multi-purpose assembly 230. Just the lid 110 of the vessel and the multi-purpose assembly are shown in transparent, perspective view in FIG. 8, and detail of the multi-purpose assembly as it is inserted through the lid is shown in transparent, perspective view in in FIG. 9.

In more detail, the multi-purpose assembly 230 has a central sparge gas tube ending at a gas outlet 232 at a delivery end of the assembly inside the vessel 100, several liquid feed tubes 234 feed liquid to respective feed channels with outlets at the delivery end of the assembly above the gas outlet, and four electrodes 202 of a capacitance probe project from the delivery end of the assembly above the gas outlets. The remote end of the assembly outside the vessel has a connector 204 configured for coupling to external devices and onward transmission of measurements made by the electrodes. Advantageously, by combining the gas sparger and liquid feeds with the capacitance probe, fewer assembly steps are needed to form the bioreactor, and better use can be made of available space in and around the vessel.

Figure 9:
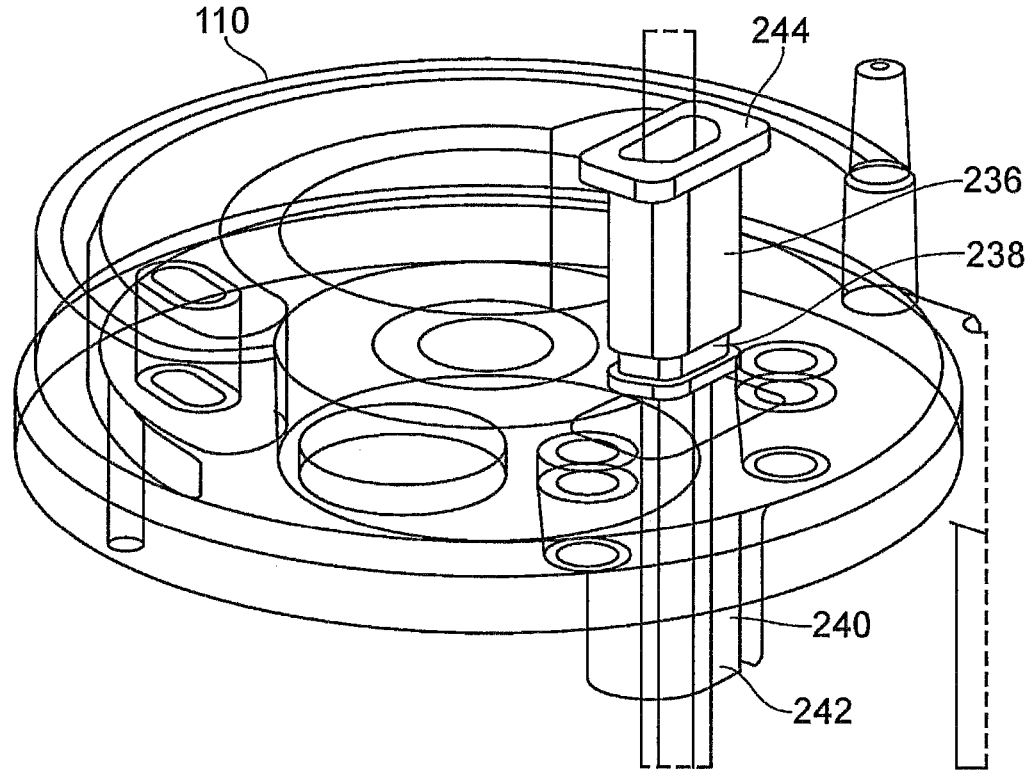
FIG. 9 shows a transparent, perspective view of detail of the multi-purpose assembly of FIGS. 7 and 8 as it passes through the lid.
Figure 10:
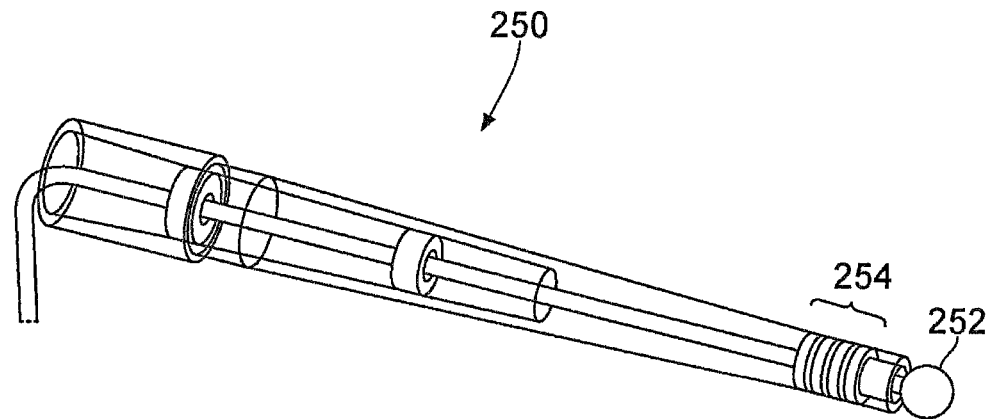
FIG. 10 shows a transparent, perspective view of a combined capacitance and pH probe.

The multi-purpose assembly 230 passes through an aperture in the lid 110, the aperture being offset from the centre of the lid. The assembly is secured to the lid by inserting the delivery end, from the top side of the lid, through a rectangular aperture formed in the lid. As best shown in FIG. 9, the assembly has a collar 236 with a matching rectangular shape to the aperture, and a circumferential recess 238 set back from a bottom end of the collar. A pair of flexible plastic members 240 extend downwardly from the lid on opposite sides of the aperture. Each of these members ends in an inwardly directed barb 238. On insertion of the assembly, the barbs slide against the outward surface of the bottom end of the collar and are bent outwardly thereby. When the barbs reach the circumferential recess, they resile back inwards, in the manner of a snap-fit connector, to secure the assembly to the lid at a predetermined insertion position.

The multi-purpose assembly 230 has a flange 244 at the top end of the collar 236, with a sealing element (not shown) being carried on the underside of the flange. The sealing element mediates an abutment of the bottom surface of the flange and a corresponding top surface of the lid 110 to prevent over-insertion of the assembly beyond the predetermined insertion position. The sealing element is also compressed by this abutment to seal the multi-purpose assembly 230 to the lid.

If the lid 110 is removed from the vessel 100, the flexible plastic members 240 are accessible on the underside of the lid, and by pulling them apart, a user can withdraw the multi-purpose assembly 230 from the lid for eventual reinsertion or substitution.

Although in this variant the capacitance probe is formed into a multi-purpose assembly with a sparge tube and liquid feed tubes, other combinations are possible. For example, the capacitance probe can be combined in a multi-purpose assembly with the pH probe. Such a combined capacitance and pH probe 250 is shown in transparent, perspective view in FIG. 10. A sensing end of the probe has a glass membrane 252 providing a glass pH electrode structure, while set back from the glass membrane are four axially-spaced, circumferential ring electrodes 254 of a capacitance probe.

8

Figure 11:
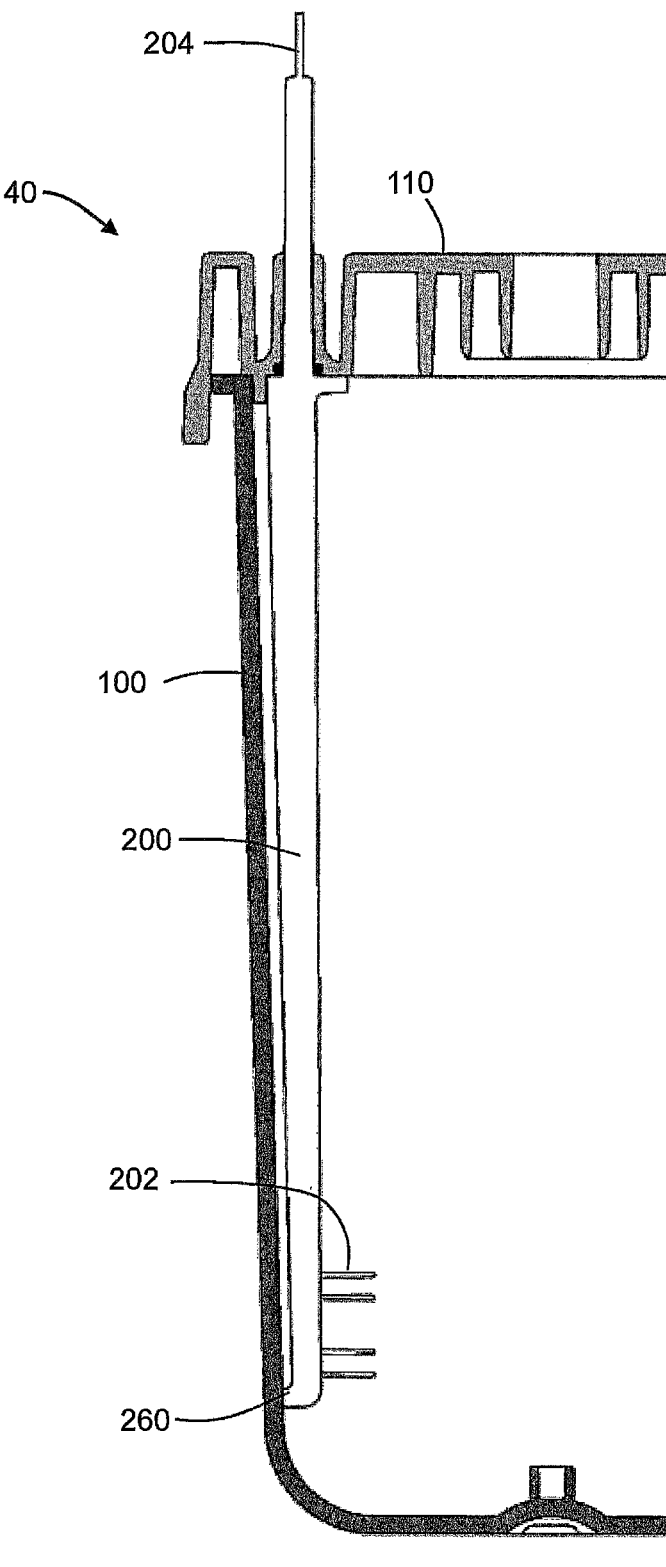
FIG. 11 shows longitudinal partial cross-section through the vessel, lid and capacitance probe of a further variant of the bioreactor.

FIG. 11 shows a longitudinal partial cross-section through the vessel 100, lid 110 and capacitance probe 200 of a further variant of the bioreactor 40. In this variant, the capacitance probe is provided with a lateral projection 260 at its sensing end and on the opposite side of the probe to the electrodes 202. The projection rests against the side wall of the vessel to enforce a predetermined minimum stand-off distance between the probe and the side wall along the length of the probe from the lid to the projection. This stand-off distance, which is typically at least 1.0 mm, helps to avoid build-up of biomass solids between the probe and the side wall. When the distance is less than 1.0 mm, undesirable accumulation of biomass solids in this location has been experimentally observed.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A bioreactor including:
a rigid-walled vessel for containing a biological medium, the vessel having a lid;
a probe passing through an aperture in the lid and having a sensing end inside the vessel and a remote end outside the vessel, the sensing end having plural electrodes for immersion in the biological medium, and the remote end being configured for coupling to external devices and transmission thereto of electrical or electromagnetic measurements made by the electrodes;
wherein one of the lid and the probe has one or more resiliently deformable mechanisms and the other of the lid and the probe has one or more respective complementary surfaces, the resiliently deformable mechanisms and the complementary surfaces being configured such that, on insertion of the probe through the aperture to assemble the probe to the lid, the one or more resiliently deformable mechanisms are first deformed on sliding against the one or more complementary surfaces and then resile when the probe reaches a predetermined insertion position relative to the lid to secure the probe to the lid; and
wherein one of the lid and the probe carries a sealing element which seals the probe to the lid when the probe is secured at the predetermined position;
wherein the probe further includes a flange on a first side of the probe and a shoulder on a second side of the probe opposite the first side, wherein the flange is offset from the shoulder along an insertion direction of the probe so the probe can adopt only one angular orientation around the insertion direction of the probe when the probe is located at the predetermined position.

2. The bioreactor according to claim 1, wherein the one or more resiliently deformable mechanisms and the one or more complimentary surfaces form a snap-fit connector.

3. The bioreactor according to claim 1, wherein the one or more resiliently deformable mechanisms are one or more flexible members or one or more spring-loaded detent mechanisms.

4. The bioreactor according to claim 1, wherein the probe and the lid are configured such that the one or more resiliently deformable mechanisms are deformable by a user to allow the probe to be withdrawn from the lid and reinserted multiple times.

5. The bioreactor according to claim 1, wherein a top surface of the flange and a bottom surface of the lid interact to prevent the probe being over-inserted beyond the predetermined position.

6. The bioreactor according to claim 5, wherein the sealing element is sandwiched between the top surface of the flange and the bottom surface of the lid and seals to the top surface of the flange and the bottom surface of the lid to seal the probe to the lid when the probe is located at the predetermined position.

7. The bioreactor according to claim 1, wherein the probe has a lateral projection at its sensing end which rests against a side wall of the vessel to enforce a minimum stand off distance between the probe and the side wall along a length of the probe from the lid to the projection.

8. The bioreactor according to claim 1, wherein the probe is part of a multi-purpose assembly inserted through the aperture in the lid, the multi-purpose assembly also containing either or both of (a) a sparger for conveying sparging gas to the biological medium, and (b) further electrodes forming a pH sensor for sensing the pH of the biological medium.

9. The bioreactor according to claim 1, wherein the lid is removably replaceable from the vessel.

10. The bioreactor according to claim 1 which is a single-use bioreactor.

11. The bioreactor according to claim 1, wherein the probe is a capacitance, impedance, permittivity or conductivity probe.

12. The bioreactor according to claim 1, wherein a first top surface of the flange and a second top surface of the shoulder cooperate with a corresponding bottom surface of the lid so the probe can adopt the only one angular orientation around the insertion direction of the probe when the probe is located at the predetermined position.

* * * * *